United States Patent
Bell et al.

(10) Patent No.: US 7,033,541 B2
(45) Date of Patent: Apr. 25, 2006

(54) BICARBONATE RECEPTOR COMPOUNDS

(76) Inventors: Thomas W. Bell, 6400 Sharlands Ave. D1022, Reno, NV (US) 89523; Jinhua Chen, 1679 Montemar Way, San Jose, CA (US) 95125; Alisher B. Khasanov, 16633 Deer Ridge Rd., San Diego, CA (US) 92127

( * ) Notice: Subject to any disclaimer, the term of this patent is extended or adjusted under 35 U.S.C. 154(b) by 135 days.

(21) Appl. No.: 10/396,004

(22) Filed: Mar. 25, 2003

(65) Prior Publication Data

US 2004/0191917 A1 Sep. 30, 2004

(51) Int. Cl.
C07D 471/22 (2006.01)
G01N 21/77 (2006.01)

(52) U.S. Cl. .................. 422/82.05; 436/128; 436/164; 436/172; 436/133; 546/26

(58) Field of Classification Search ................ 436/172, 436/93–95, 127–132; 546/26, 27, 32
See application file for complete search history.

(56) References Cited

U.S. PATENT DOCUMENTS

| | | | |
|---|---|---|---|
| 3,501,473 A | 3/1970 | Bell | 260/256.4 |
| 5,030,728 A | 7/1991 | Bell | 546/27 |
| 5,128,466 A | 7/1992 | Bell | 540/452 |
| 5,283,333 A | 2/1994 | Bell | 546/27 |
| 6,566,086 B1 | 5/2003 | Al Athel et al. | 435/17 |

FOREIGN PATENT DOCUMENTS

| | | |
|---|---|---|
| EP | 1 067 384 A2 | 6/2000 |
| EP | 1 067 384 A3 | 6/2000 |
| WO | WO 01/55719 A2 | 8/2001 |
| WO | WO 01/55719 A3 | 8/2001 |
| WO | WO 02/14465 A2 | 2/2002 |

OTHER PUBLICATIONS

Tamaru, S. et al. "Circular dichroism readout of sugar recognition in the cleft of a fused-pyridine receptor" PNAS, vol. 99(8), pp. 4972-4976, Apr. 16, 2002.*
Bell, S.C., Gochman, C., Wei, P.H.L., "Syntheses of Heterocyclic Fused Thiazolecarboxylic Acids I", Research Division, Wyeth Laboratories Inc., Jul. 28, 1975, pp 1207-1210.
Bell, T.W., Beckles, D.L., Debetta, M. Glover, B.R., Hou, Z., Hung, K.Y., Khasanov, A.B., "An Improved Preparation of 4-Aminopyrimidine-5-Carboxaldehyde", Organic Preparations and Procedures Int., 34(4), 359-000 (2002).
Bell, T.W., Khasanov, A.B., Drew, M.G.B., "Role of Pyridine Hydrogen-Bonding Sites in Recognition of Basic Amino Acid Side Chains", Journal of the American Chemical Society, vol. 124, No. 47, 14092-14103 (2002).
Bell, T.W., Khasanov, A.B., Drew, M.G.B., Filikov, A., James, T.J., "A Small-Molecule Guanidinium Receptor: The Arginine Cork", Agnew. Chem. Int. Ed., 1999, 38, No. 17, 2543-2547.
Chicharro, J.L., Prados, P., deMendoza, J., "Synthesis and Self Association of 4,7-Diamino-2, 9-dimethyl-5, 6, 11a-tria-6,11,11a,12-tetrahydronaphthacene Derivatives as Dibenzoguanidine Receptors for Oxoanion Recognition", J. Chem. Soc., Chem. Commun., 1994, pp 1193-1194.
Dehmlow, E.V., Dehmlow, S.S., "Phase Transfer Catalysis", Verlag Chemie, 1983, pp 1-24.
Jaffe, E.E., Matrick, H., "Synthesis of Epinodolidione", The Journal of Organic Chemistry, vol. 33, No. 11, 1968, pp 4004-4010.
Keller, W.E., "Compendium of Phase-Transfer Reactions and Related Synthetic Methods", Fluka AG, CH-9470 Buchs. 1979, 1-25.
Khasanov, A.B., "Water-Soluble Receptors for Hydrogen-Bonding Guests", Dissertation from University of Nevada, Reno, Aug. 2000.
Leiner, M.J.P., "Optical sensors for in vitro blood gas analysis", Sensors and Actuators, B 29 (1995) 169-173.
Lissel, M., Dehmlow, E.V., "Phasentransfer-katalytische Herstellung von Kohlensaureestern ohne Verwendung von Phosgen", Chem. Ber. 114 (1981), 1210-1215.
Molina, P., Alajarin, M., Vidal, A., "Preparation of [5,6,6] Tricyclic Guanidines from C,C-Bis(iminophosphoranes)", Tetrahedron, vol. 51, No. 18, pp 5351-5360, 1995.
Molina, P., Alajarin, M., Vidal, A., "Synthetic Applications of Bis (iminophosphoranes). One-Pot Preparation of Rigid Bicyclic Guanidines", J. Org. Chem. 1993, 58, 1687-1695.
Tominaga, Y., Michioka, T., Moriyama, K., Hosomi, A., "Synthesis of Quinoline Derivatives Using Ketene Dithioacetals", J. Heterocyclic Chem, 27, 12171225, (1990).

* cited by examiner

*Primary Examiner*—Jeffrey R. Snay
(74) *Attorney, Agent, or Firm*—Roche Diagnostics Operations, Inc.

(57) ABSTRACT

The present invention relates to compounds and more particularly to compounds which are useful for the determination of bicarbonate and the delivery of bicarbonate to a non-aqueous solution. The invention further relates to an optical sensor for the determination of bicarbonate in a liquid sample.

12 Claims, 7 Drawing Sheets

BICARBONATE RECEPTOR COMPOUNDS

The present invention relates to compounds and more particularly to compounds which are useful for the determination of bicarbonate and the delivery of bicarbonate to a non-aqueous solution. The invention further relates to an optical sensor for the determination of bicarbonate in a liquid sample.

BACKGROUND OF THE INVENTION

Bicarbonate is a major constituent of water and wastewater. The acid-base balance in the human body is regulated by pulmonary and renal mechanisms. Bicarbonate is the main ion connecting these two regulative mechanisms.

A conventional method for the determination of bicarbonate ion is of measuring the partial pressure of carbon dioxide in a liquid and hydrogen ion concentration. The concentration of bicarbonate ion can be determined by calculating from the above values. However, the method is disadvantageous in the simultaneous measurement of the partial pressure of carbon dioxide and pH of the liquid.

Another conventional method is of utilizing the conversion of bicarbonate ion into carbon dioxide in acidic conditions, and measuring the volume of the evolved carbon dioxide. In general, a large scale equipment is necessary for measuring the volume of gas accurately, and accordingly, this method is disadvantageous to the measurement of a large number of samples.

There are three clinically approved methods to measure bicarbonate ion in blood, serum and plasma samples. The first approach is the calculation of bicarbonate concentration from measured pH and $pCO_2$ levels. Mainly this is done using the Henderson-Hasselbalch equation. The second method is calculation of the base excess/deficit from $pCO_2$ and pH. The idea of base excess/deficit is based on the premise that the degree of deviation from the normal buffer availability can be calculated independently of $CO_2$ changes. The third method is determination of the calculated pH difference from measured pH and $pCO_2$.

Compounds of the type capable of forming complexes with analyte molecules like urea, thiourea, guanidine, substituted guanidines, arginine, amidine compounds, creatinine are known from WO 01/55719 A, WO 02/14465 A, U.S. Pat. No. 5,283,333 A and U.S. Pat. No. 5,030,728 A. The compounds are characterized by the structural element

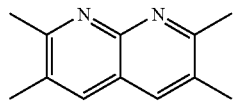

Structural elements of the type —C=N—C=N— are able to bind two hydrogen atoms of an analyte molecule via hydrogen-bridge bonds (compare structure VIa in U.S. Pat. No. 5,030,728). The analyte molecules possess at least two hydrogen atoms in close vicinity, able to bind to the above structural element.

In contrast, bicarbonate possesses a single hydrogen atom and three oxygen atoms.

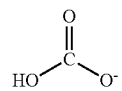

In sum, the oxygen atoms possess seven lone electron pairs, of which five are located in the molecular plane and are able to bind hydrogen of "hydrogen bond donors" in a planar host compound via hydrogen bridge-bonds. Further, bicarbonate possesses one hydrogen atom, able to bind to one "hydrogen bond acceptor". Thus, it is obvious that, due to its steric positions of hydrogen bond donors and acceptors, the structural elements (i.e., —C=N—C=N—) known in the art are not suitable to selectively bind bicarbonate.

Moreover, the host compounds of the prior art possess electron-rich cavities that bind only neutral and cationic guest molecules, whereas, in order to bind anions such as bicarbonate, the host compound must feature a sufficient number and correct orientation of hydrogen bond donor groups.

Bicarbonate is known to have low solubility in non-aqueous solutions or solvents. For some applications, however, it is necessary or advantageous to introduce bicarbonate in non-aqueous solutions. For example, bicarbonate can be utilized as a catalyst or a buffer in organic solvents. Further applications involve the use of bicarbonate as a base or simply as a reagent in chemical reactions.

Over the past 30 years, chemists have used phase transfer agents to solubilize polar reactants such as hydroxide in order to conduct useful reactions in organic solvents (W. E. Keller, Compendium of Phase-Transfer Reactions and Related Synthetic Methods, Fluka AG (Buchs, Switzerland, 1979); E. V. Dehmlow, S. S. Dehmlow, Phase Transfer Catalysis, Verlag Chemie (Weinheim, Germany, 1983)). Conventional phase transfer agents such as crown ethers and quaternary ammonium salts either bind the cation, e.g. sodium, to solubilize the anion as an ion pair, or they replace the hydrophilic cation with a lipophilic one. Because they do not selectively bind the anion, they cannot select a single anion for transport from water into the organic layer, if more than one anion is present.

Carbonate has been used as a base in many phase-transfer reactions (see the references above), but carbonate is so strongly hydrated that there is doubt that it is actually transported into the aqueous layer. Such reactions may actually occur at the solid-liquid or liquid-liquid interface. It has also been proposed that bicarbonate actually mediates these reactions, because it is less polar than carbonate and is present in equilibrium in the aqueous solution (E. Lissel, E. V. Dehmlow, Chem. Ber. 114, 1210 (1981)). A phase transfer agent that is specific for bicarbonate would resolve this problem.

Therefore, there is a need for compounds that selectively form complexes with bicarbonate, enabling the measurement of bicarbonate levels in body fluids and other liquids. There is also a need for phase-transfer agents which are capable of delivering bicarbonate to non-aqueous solutions.

Accordingly, it is an object of the present invention to provide compounds which are suitable as receptor compounds that reversibly bind bicarbonate.

Another object of the invention is to provide compounds which allow to determine bicarbonate levels in liquid samples, preferably by means of photometric methods.

A further object of the invention is to provide compounds which are suitable for the manufacture of optical sensors.

It is a further object of the invention to provide an optical sensor for the determination of bicarbonate in a liquid sample.

A further object of the invention is to provide compounds which are useful as phase-transfer agents for the delivery of bicarbonate to non-aqueous solutions.

SUMMARY OF THE INVENTION

The present invention provides compounds having the general formula I wherein
- $A_1$ and $A_2$ are selected from the group consisting of carbon (=CH—) and nitrogen (=N—);
- $D_1$ and $D_2$ are selected from the group consisting of —OH, —SH and —NHR$^1$ groups, wherein R$^1$ is hydrogen, hydrophilic substituent, hydrophobic substituent or linker;
- $X_1$ and $X_2$ are selected from the group consisting of oxygen (=O), sulphur (=S) and =NR$^2$ group, wherein R$^2$ is hydrogen, hydrophilic substituent, hydrophobic substituent or linked;
- $X_3$ is selected from the group consisting of oxygen (=O), sulphur (=S), =NR$^2$ group and two singly bonded moieties, wherein both moieties are hydrogen or one moiety is hydrogen and the other moiety is selected from the group of hydrophilic substituent, hydrophobic substituent and linker; and
- $R_1$–$R_9$ are selected from the group consisting of hydrogen, electron donating substituent, electron accepting substituent, hydrophilic substituent, hydrophobic substituent and linker, or $R_3$ and $R_4$ and/or $R_6$ and $R_7$ form together an aromatic or heteroaromatic, substituted or unsubstituted ring and the remaining moieties $R_1$–$R_9$ are as defined above.

The present invention also provides an optical sensor for the determination of bicarbonate in a liquid sample, comprising a water impermeable light transmissive support, a hydrophilic ion permeable indicator layer thereupon and optionally a hydrophilic ion permeable light-blocking layer, wherein the indicator layer incorporates a compound having the above formula I.

DETAILED DESCRIPTION OF THE INVENTION

Figure 1:
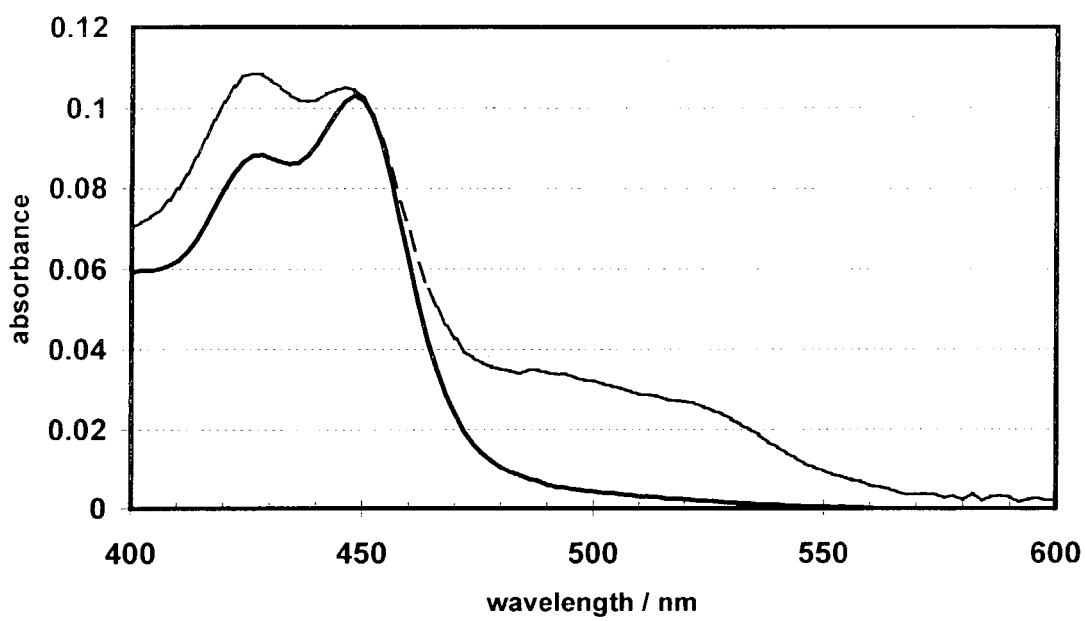
FIG. 1 illustrates the UV-visible absorption spectra of a compound JCb according to the invention in methanol prior to (bold line) and after (thin line) complexation of bicarbonate.

In accordance with the present invention, compounds are provided having the general formula I wherein
- $A_1$ and $A_2$ are selected from the group consisting of carbon (=CH—) and nitrogen (=N—);
- $D_1$ and $D_2$ are selected from the group consisting of —OH, —SH and —NHR$^1$ groups, wherein R$^1$ is hydrogen, hydrophilic substituent, hydrophobic substituent or linker;
- $X_1$ and $X_2$ are selected from the group consisting of oxygen (=O), sulphur (=S) and =NR$^2$ group, wherein R$^2$ is hydrogen, hydrophilic substituent, hydrophobic substituent or linker;
- $X_3$ is selected from the group consisting of oxygen (=O), sulphur (=S), =NR$^2$ group and two singly bonded moieties, wherein both moieties are hydrogen or one moiety is hydrogen and the other moiety is selected from the group of hydrophilic substituent, hydrophobic substituent and linker; and
- $R_1$–$R_9$ are selected from the group consisting of hydrogen, electron donating substituent, electron accepting substituent, hydrophilic substituent, hydrophobic substituent and linker, or $R_3$ and $R_4$ and/or $R_6$ and $R_7$ form together an aromatic or heteroaromatic, substituted or unsubstituted ring and the remaining moieties $R_1$–$R_9$ are as defined above.

These compounds are capable of reversibly binding bicarbonate. The bicarbonate receptor provides—in adequate steric and conformational positions—structural elements for binding one hydrogen atom and 3–5 structural elements for binding oxygen lone electron pairs. The binding structure of the reversible bicarbonate complex is shown below with a preferred embodiment of a compound according to the invention, which is able to bind 1 hydrogen atom and 3 lone electron pairs of bicarbonate.

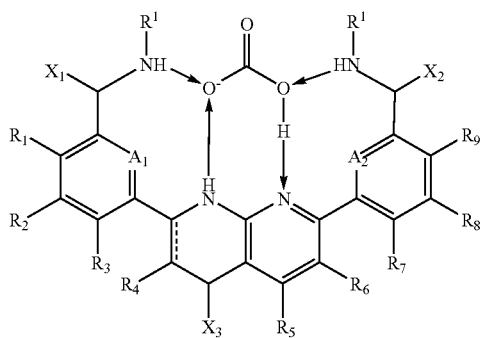

The arrows indicate hydrogen bridge-bonds. The atoms forming the hydrogen bridge bonds must be in favorable conformational and steric positions.

Suitable structural elements "hydrogen bond donors" of receptor molecules, able to bind lone pairs of analyte (guest) molecules include —NH—, —OH and —SH. A suitable structural element "hydrogen bond acceptors" of receptor molecules, able to bind hydrogen atoms (i.e., from —OH) of analyte (guest) molecules is —N=.

Hydrophilic substituents to be utilized in the present invention are any hydrophilic functional groups capable of improving the water solubility of the compound. The hydrophilic functional groups can be directly attached to the non-bicarbonate binding atoms of the structure and are characterized by a short chain containing carbon, hydrogen and heteroatoms (e.g., sulfur, oxygen, and nitrogen). Representative examples of hydrophilic substituents include, but are not limited to, the following functional groups: alcohols, amines, carboxylic acids, carboxylates, amides, sulfamides, sulfonic acids, sulfonates, sulfates, esters, thiol esters, ethers, thiols, thiolates, thioethers, and combinations thereof.

Hydrophobic substituents to be utilized in the present invention are any hydrophobic functional groups, capable of improving the solubility in non-watery environments (i.e., organic solvents, non-hydrophilic polymers and particles). The hydrophobic functional groups can be directly attached to the non-bicarbonate binding atoms of the structure and are characterized by a carbon chain with two to twenty carbons being preferred. The carbon chain can be substituted or unsubstituted, saturated or unsaturated, and contain saturated, unsaturated or aromatic ring structures (e.g., cyclohexane, benzene, naphthalene, etc.), or nonpolar functional groups (e.g. ether, thioether, ester or alkyl halide, preferably chloride or fluoride).

In the context of the present invention, linker means a reactive group for attachment of the compound to a carrier matrix. Reactive substituents to be utilized for covalent attachment of the compound to surfaces or matrices such as ion-exchange resins, particles such as cellulosic fibers, porous glass, silica gel, and polymeric compounds such as hydrophillic synthetic materials (i.e., polvinylalcohols, polyurethanes, polyacrylamides and polyvinylpyrrolidone) are known in the art. Preferred examples include, but are not limited to, amides, esters, ethers, and disulfides optionally with a short carbon chain.

Examples of electron donating groups include, but are not limited to, amino, alkylamino, dialkylamino, hydroxy, alkoxy, acylamino, thiol and alkanethiol.

Examples of electron withdrawing or accepting groups include, but are not limited to, nitro, cyano, chloro, bromo, iodo, fluoro, acyl, carboxyl, alkoxycarbonyl and acyloxy.

It may also be advantageous to incorporate positively charged groups as substituents to stabilize the host-guest complex by electrostatic attraction.

In a preferred embodiment, the present invention provides a compound having general formula II

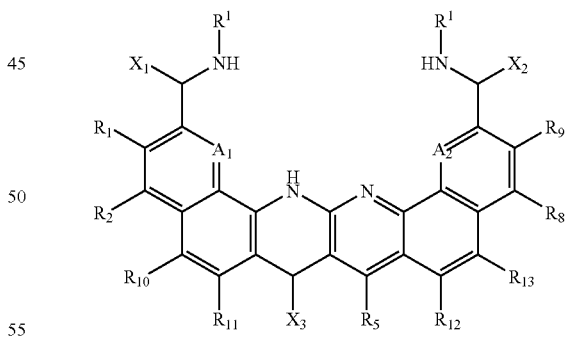

wherein $R_{10}$–$R_{13}$ are selected from the group consisting of hydrogen, electron donating substituent, electron accepting substituent, hydrophilic substituent, hydrophobic substituent and linker.

In a preferred embodiment $X_1$, $X_2$, and $X_3$ are oxygen and $R_1$, $R_2$, $R_5$, $R_8$, $R_9$ and $R_{10}$-$R_{13}$ are hydrogen (see general formula III).

In another preferred embodiment $A_1$ and $A_2$ are nitrogen and R$^1$ is selected from the group consisting of —C$_4$H$_9$, —CH$_2$CH$_2$OH, —C$_8$H$_{17}$ and —CH$_2$CH$_2$NH$_2$.

In another preferred embodiment $X_1$, $X_2$, and $X_3$ are oxygen, $A_1$ and $A_2$ are nitrogen, $R_1$, $R_2$, $R_5$, $R_8$, $R_9$ and $R_{10}$–$R_{11}$ are hydrogen, $R^1$ is —$C_4H_9$, $R_{12}$ is hydrogen, an electron donating group or an electron withdrawing group and $R_{13}$ is an electron donating group or an electron withdrawing group (see general formula VI).

In a particular embodiment $R_{12}$ is selected from the group consisting of hydrogen, —$NH_2$, —NHR', —OH, —OR', —SH, —SR', —CN, —OAc, —Cl and —$NO_2$ and $R_{13}$ is selected from the group consisting of —$NH_2$, —NHR', —OH, —OR', —SH, —SR', —CN, —OAc, —Cl and —$NO_2$, wherein R' is alkyl group, aryl group or linker.

In a more particular embodiment $R_{12}$ is hydrogen and $R_{13}$ is a —$NO_2$ group.

In another more particular embodiment $R_{12}$ is a —$NO_2$ group and $R_{13}$ is hydrogen.

In a further preferred embodiment, the present invention provides a compound, wherein $D_1$ and $D_2$ are —$NHR^1$ groups (see general formula IV).

In a preferred embodiment $X_1$, $X_2$, and $X_3$ are oxygen, $A_1$ and $A_2$ are nitrogen and $R_1$–$R_9$ are hydrogen (see general formula V).

The compounds according to the present invention also allow to determine bicarbonate levels in liquid samples. In accordance with the invention, the compounds are designed to produce an optical signal, i.e. the bound (complexed) and non-bound (non-complexed) compounds differ in their optical properties and thus allow the determination of bicarbonate.

Preferred embodiments of compounds for the determination are those having general formulas II, III and VI.

In order to determine the bicarbonate level in liquid samples, the compound of the present invention can be present in dissolved or dispersed form (i.e., bound to a carrier particle). It can be present immobilized on an appropriate carrier, for example a test strip. The compound can be directly contacted with a sample containing bicarbonate in which the compound of the present invention and bicarbonate in the sample form a complex. The compound can also be indirectly contacted with a sample containing bicarbonate. For example, the compound can be present in a matrix which is brought in direct contact with the liquid sample. It then reacts in the matrix with bicarbonate diffusing from the sample into that matrix. The determination of the bicarbonate level involves measuring an optical signal for the compound of the invention due to complex formation.

"Optical signal" in the context of the invention means any type of optical property for the compound that can be measured, such as light absorption or emission (i.e., luminescence). Preferably, the compounds according to the invention are utilized for the photometric determination of bicarbonate in liquids, i.e. determination by means of light absorbance and fluorescence. For example, the compounds of the invention may be applied in the photometric determination of intracellular bicarbonate inside biological cells.

Measuring the optical signal entails measuring the optical signal of bound and unbound compounds. Once the optical signal is measured, the method further includes correlating the optical signal to the concentration of bicarbonate in the sample following techniques known in the art, thus providing a method of detecting and quantitating bicarbonate in a liquid sample. As will be apparent to one skilled in the art, the optical signal provided by the compound of the invention will vary with the choice of electron donating/accepting substituents.

The sensing method as described above is simple and can be performed with inexpensive apparatus. The sensing method can be adapted for use with large equipment performing multiple analysis, yet can also be employed with inexpensive stand alone instruments for emergency use close to the bed side.

The compounds according to the present invention are also useful as phase-transfer agents for the delivery of bicarbonate to non-aqueous solutions. In particular, where bicarbonate is applied as a catalyst, a buffer, a base or a reagent, the compounds of the present invention can advantageously be used. It will be appreciated that the substituents of the compounds may be selected in order to enhance solubility of the compound in the particular solvent of interest, e.g. hydrophobic alkyl or aryl groups for hydrocarbon and chlorocarbon solvents, or fluorinated alkyl groups for fluorocarbon solvents.

Moreover, the bicarbonate complex of the compounds according to the invention could be used stoichiometrically to provide a controlled amount of bicarbonate or carbon dioxide for reactions in organic solvents.

In a preferred embodiment, the compounds of the invention are used in the manufacture of optical sensor elements for determining bicarbonate levels in non-biological and biological fluids. Preferred biological fluids are whole blood, serum, plasma or urine, for example.

The present invention also provides an optical sensor for the determination of bicarbonate in a liquid sample. In accordance with the invention, the optical sensor comprises a water impermeable light transmissive support, a hydrophilic ion permeable indicator layer thereupon and optionally a hydrophilic ion permeable light-blocking layer, wherein the indicator layer incorporates a compound according to the above described aspect of the invention.

Figure 12:
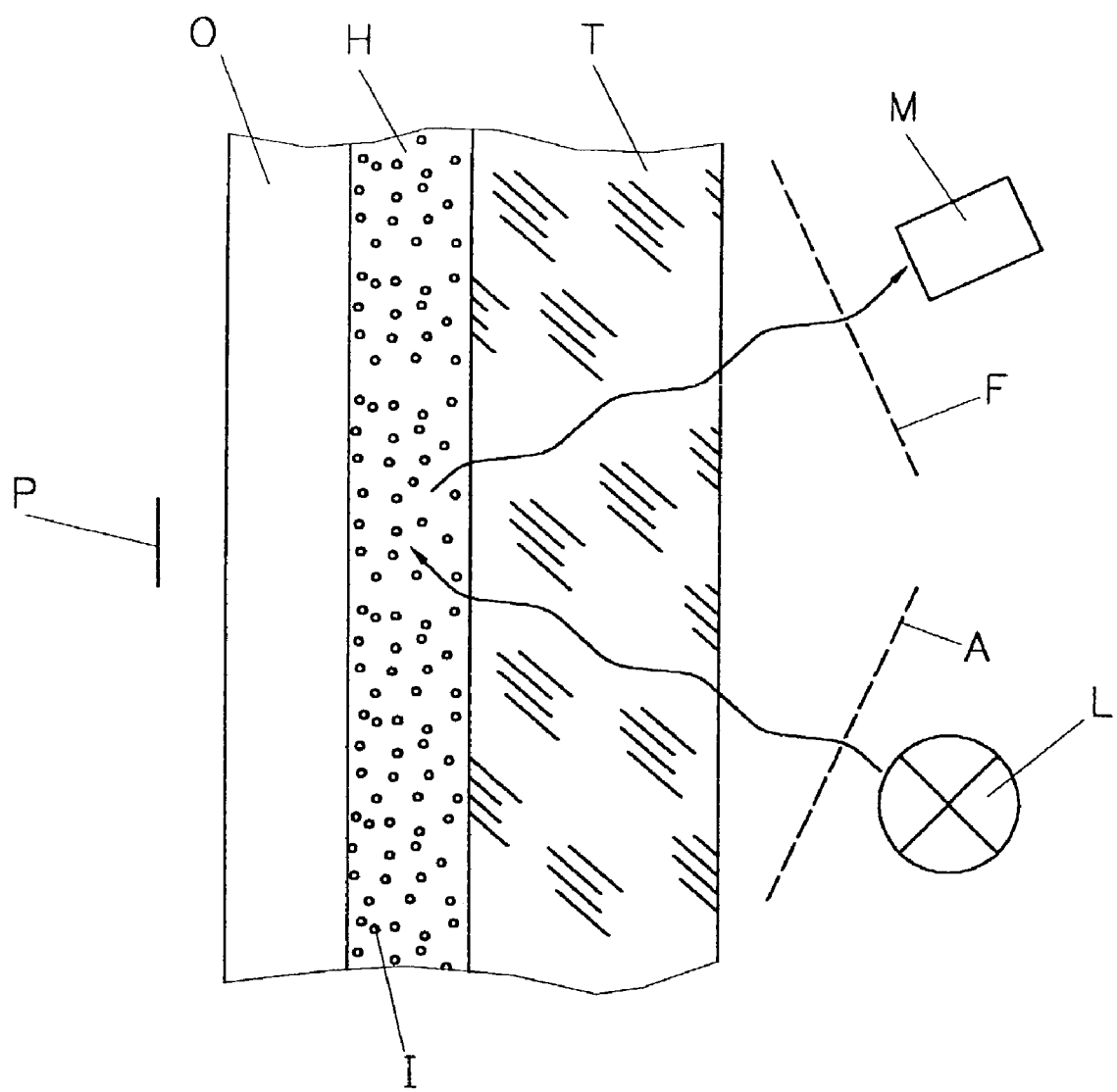
FIG. 12 depicts a schematic illustration of an embodiment of an optical sensor according to the invention.

A preferable optical sensor element comprises a layer construction composed of a support and one or two hydrophilic water and ion permeable layers (see FIG. 12). The support (T) can be a water-impermeable light transmissive transparent support, for instance a plastic support, a film or sheet. In a particular embodiment the support can be the distal end of a fiber-optic light guide.

The water and ion-permeable layers are indicator layer (H) and light-blocking layer (O). On the support, the indicator layer is provided directly or through an adhesive layer. The indicator layer is a hydrophilic water-absorptive, water and ion permeable layer wherein the compound of the invention (=optical indicator (I)) is incorporated. The indicator layer can be any hydrophilic ion-permeable substance capable of incorporating the bicarbonate receptor, as long as this layer is insoluble in water and physiological fluids. Illustrative of the indicator layer are synthetic or modified naturally-occurring polymers, such as hydrophilic polyvinyl alcohols, polyurethanes, polyacrylamides and other such crosslinked or non-crosslinked hydrophilic polymers. Hydrophilic and ion permeable with regard to the substance used means that the material contains sufficient water to allow in/out diffusion of bicarbonate and a counter ion (i.e., small cations such as $Na^+$, $K^+$, $Ca^{2+}$).

A light-blocking layer can optionally be provided on top of the indicator layer. The light-blocking layer is a hydrophilic, water-absorptive and ion-permeable layer wherein light-absorptive or light-reflecting (called "light-blocking" collectively) particles are dispersed. The light-blocking layer protects from any optical interferences with the sample (P). In a preferred embodiment, indicator layer and light-blocking layer consist of same basic polymer.

The optical measuring means may consist of a LED as a light source L, a photodiode M as a detector, optical filters A and F for selecting the wavelengths, an optical arrangement for conducting the excitation light into layer H and for conducting the emission light to photodiode M as well as a means for signal processing (not represented). On the side of the excitation, an interference filter and on the side of the emission, a cut-off filter may be used.

Optical-chemical sensors and methods of production are well known in the art, such as for example from M. Leiner, Sensors and Actuators B 29, 169–173, 1995 "Optical sensors for in vitro blood gas analysis", which is encorporated herein by reference.

The compounds of the present invention can be synthesized following techniques known in the art as illustrated by the examples set forth below. Accordingly, one skilled in the art can synthesize the compounds of the invention following the teachings of the examples.

EXAMPLES

The following non-limiting examples illustrate the synthesis, characterization and utility of the compounds of the present invention.

Appended Scheme 1 depicts a general reaction scheme for the preparation of preferred embodiments of the invention. The steps leading to intermediate 13 of the scheme are described in "A Small-Molecule Guanidinium Receptor: The Arginine Cork", T. W. Bell et al., Angew. Chem. 111, 2705–2709 (1999) or Angew. Chem. Int. Ed. Engl. 38, 2543–2547 (1999) and "An Improved Preparation of 4-Aminopyrimidine-5-carboxaldehyde", T. W. Bell et al., Org. Prep. Proc. Int. 34, 321–331 (2002) which are incorporated in their entirety by reference herein.

Example 1

Synthesis of Diester 14

A 100-mL single-necked, round-bottomed flask equipped with a magnetic stirring bar and a reflux condenser fitted with nitrogen gas inlet was charged with 0.48 mg (1 mmol) of diester 1, 50 mL of bromobenzene, and then 2.27 g (10 mmol) of 2,3-dichloro-5,6-dicyano-1,4-quinone (DDQ). The resulting suspension was heated by means of a 100° C. oil bath and stirred under nitrogen for 72 h. Then the solvent was evaporated by rotary evaporation. A solution of the resulting residue in 50 mL of $CHCl_3$/MeOH (99/1) was filtered through alumina adsorption (Fisher, 80–200 mesh, 20 g), which was washed with 200 mL of $CHCl_3$/MeOH (99/1). Then the alumina was transferred to a Soxhlet extractor and extracted with hot $CHCl_3$/MeOH (90/10) for three days. The extract was combined with the solution from the alumina filtrates. After the solvent was evaporated, the residue was purified further by column chromatography (silica gel, 32–63 μM, $CHCl_3$/MeOH (97/3-90/10). A total of 0.18 g (43% yield) of product 14 was obtained together with 73 mg of recovered starting material. $^1$H-NMR (300 MHz, $CDCl_3$): δ 11.53 (s. 1H, NH), 9.48 (s, 1H, H7), 8.58 (d, J=9.2 Hz, 1H, H12 or H3), 8.57 (d, J=8.4 Hz, 1H, H3 or H12), 8.46 (m, 3H, H4, H9, H11), 8.12 (d, J=8.8 Hz, 1H, H6), 7.83 (d, J=8.8 Hz, 1H, H10), 7.69 (d J=8.8 Hz, 1H, H5), 4.64 (m, 4H, $CH_2$), 1.67 (t, J=7.1 Hz, 3H, $CH_3$), 1.58 (t, J=6.8 Hz, 3H, $CH_3$).

Synthesis of Receptor JCb

A 5-mL single-necked, round-bottomed flask equipped with a magnetic stirring bar and fitted with nitrogen gas inlet was charged with 6.4 mg of diester 14 and 2.0 mL of n-butylamine. The mixture was stirred at room temperature overnight. Then the excess n-butylamine was removed by rotary evaporation. The residue was purified by column chromatography (alumina, $CHCl_3$/MeOH (99/1)) to give 5.4 mg (38%) as a yellow solid JCb. $^1$H-NMR (300 MHz, $CDCl_3$): δ 11.27 (s, 1H), 9.23 (s, 1H), 9.22 (s, 1H), 8.89 (m, 1H, NHBu-n), 8.54 (m, 3H), 8.31 (m, 3H), 7.74 (d, 1H), 7.58 (d, 1H), 7.42 (d, 1H), 3.68 (m, 4H), 1.85 (m, 4H), 1.55 (m, 4H), 1.06 (m, 6H). Mass spectrum (70 eV, EI, quadrupole), m/z: 547.4(M+1), 433.5, 419.5, 347.3.

Synthesis of TBS Protected Ethanolamine

TBS Protected Ethanolamine=2-(t-butyldimethylsilyloxy)ethylamine

A 500-mL single-necked, round-bottomed flask equipped with a magnetic stirring bar and fitted with nitrogen gas inlet was charged with 3.06 g (50 mmol) of ethanolamine, 23.0 mL (16.7 g, 165 mmol) of triethylamine, 34.0 mg (0.27 mmol) of 4-dimethylaminopyridine (DMAP), 250 mL of anhydrous methylene chloride and 9.11 g (60 mmol) of tert-butyldimethylsilyl chloride. The mixture was stirred at room temperature for 24 h. Then 200 mL of water was added and the mixture was stirred vigorously for 1.5 h. The organic solution was separated, washed with 100 mL of water and 100 mL of brine and dried over sodium sulfate. After the solvent was removed by rotary evaporation, 7.88 g (90%) of product was obtained as a colorless liquid. $^1$H-NMR (300 MHz, $CDCl_3$): δ 3.61 (t, 2H), 2.76 (t, 2H), 1.50 (br, 2H), 0.89 (s, 9H), 0.06 (s, 6H).

Reaction of Diester 14 with TBS Protected Ethanolamine

A 5-mL single-necked, round-bottomed flask equipped with a magnetic stirring bar and fitted with nitrogen gas inlet was charged 50.3 mg (0.1 mmol) of diester 14 and 1.0 mL of TBS protected ethanolamine. The mixture was stirred at room temperature for 24 h. Then it was stirred and heated by means of a 40° C. oil bath for 10 h. The excess TBS protected ethanolamine was removed by rotary evaporation. The residue was purified by column chromatography (alumina, $CHCl_3$/MeOH (99/1)) to give 70.8 mg of product (92%) as a yellow solid. $^1$H-NMR (300 MHz, $CDCl_3$): δ 11.75 (s, 1H), 9.42 (s, 1H), 9.07(m, 1H), 8.91 (m, 1H), 8.51 (m, 5H), 8.00 (d, 1H), 7.76 (d, 1H), 7.65 (d, 1H), 4.02(m, 4H), 3.80 (m, 4H), 0.84 (s, 6H), 0.09 (s, 9H).

Synthesis of Receptor JCc

A 5-mL single-necked, round-bottomed flask equipped with a magnetic stirring bar and fitted with nitrogen gas inlet was charged with 21.6 mg (29 μmol) of diamide, 40 μL (40 μmol) of 1.0 M TBAF/THF and 1.0 mL of anhydrous THF. After the mixture was stirred at room temperature for 4 h, another 20 μL (20 μmol) of 1.0 M TBAF/THF was added. The mixture was stirred overnight. After the solvent was removed under reduced pressure, the residue was purified by column chromatography (alumina, $CHCl_3$/MeOH (99.5/0.5 to 99/1)) to give 4.9 mg (33% yield) of product JCc.

Synthesis of Receptor JCd

A 5-mL single-necked, round-bottomed flask equipped with a magnetic stirring bar and fitted with nitrogen gas inlet was charged with 44.1 mg (90 μmol) of diester 14 and 2.0 mL of octylamine. The mixture was stirred at room temperature overnight. After the excess octylamine was removed under reduced pressure, the residue was purified by column chromatography (silica gel, CHCl$_3$/acetone (80/20), then CHCl$_3$/CH$_3$OH (96/4)) to give 49.5 mg of product JCd (84%) as a yellow solid. $^1$H-NMR (300 MHz, CDCl$_3$): δ 11.2 (s, 1H), 9.13 (s, 1H), 9.02 (t, 1H), 8.54 (m, 2H), 8.42 (d, 1H), 8.22 (d, 1H), 8.14 (m, 2H), 7.50 (d, 1H), 7.39 (d, 1H), 7.23 (d, 1H). Mass spectrum (70 eV, EI, quadrupole), m/z: 659.5(M+1), 410.2, 362.2, 347.3.

Synthesis of Receptor JCe

A 5-mL single-necked, round-bottomed flask equipped with a magnetic stirring bar and fitted with nitrogen gas inlet was charged with 54.2 mg (110 μmol) of diester 14 and 1.0 mL of ethylenediamine. The mixture was stirred under nitrogen for 3 h. After the excess ethylenediamine was removed by rotary evaporation, the residue was dissolved in 15 mL hot chloroform/methanol (1/1). Hexane was added dropwise until the solution turned to slightly clouded. The solution was allowed to stand overnight. The solid was filtered to give 51.2 mg (89%) of JCe as a yellow solid. $^1$H-NMR (300 MHz, CDCl$_3$+CD$_3$OD): 9.30 (s, 1H), 8.34 (m, 5H), 7.91 (d, 1H), 7.67 (d, 1H), 7.51 (d, 1H), 3.65 (t, 4H), 3.03 (t, 4H) Mass spectrum (70 eV, EI, quadrupole), m/z: 521.3 (M+1), 307.3, 289.2, 282.4.

Example 2

Complexation Studies of Compound JCb with Bicarbonate

UV-visible absorbance and fluorescence were examined. UV absorption spectra were recorded on a Hewlett-Packard 8452A diode array UV-vis spectrophotometer, using a cell of 1 cm pathlength. Fluorescence spectra were recorded on a Photon Technology International QM-1 Steady State Fluorescence system.

Figure 2:
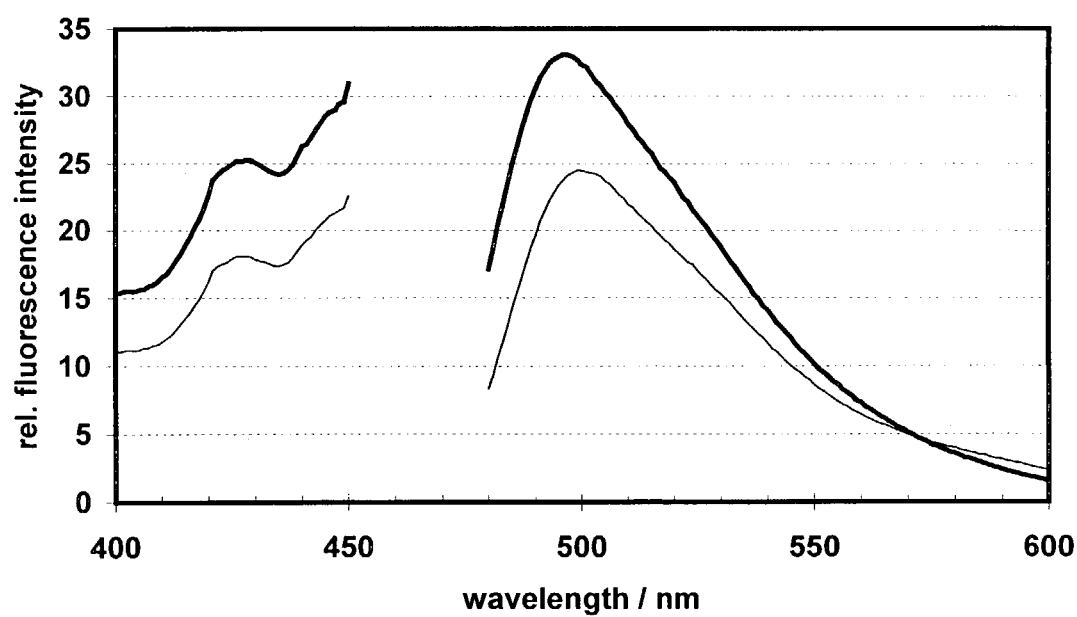
FIG. 2 illustrates the fluorescence spectra of the compound of FIG. 1 in methanol prior to (bold line) and after (thin line) complexation of bicarbonate. Excitation spectra: 400–450 nm, emission 475 nm; emission spectra: 480–600 nm; excitation 451 nm.

A sample of 0.9 mg of JCb was dissolved in 100 mL of methanol. The UV-visible absorption (FIG. 1) and fluorescence (FIG. 2) spectra were taken. An excitation wavelength of 451 nm was used to obtain the emission spectra and an emission wavelength of 475 nm was used to obtain the fluorescence spectra. Then 113.0 mg of sodium bicarbonate was added. The mixture was sonicated for 15 min and allowed to stand for one hour. Then the UV-visible absorption and fluorescence spectra were taken again. A 26% decrease in fluorescence intensity was observed.

Example 3

Complexation Studies of Compound JCc with Bicarbonate in Methanol

Figure 3:
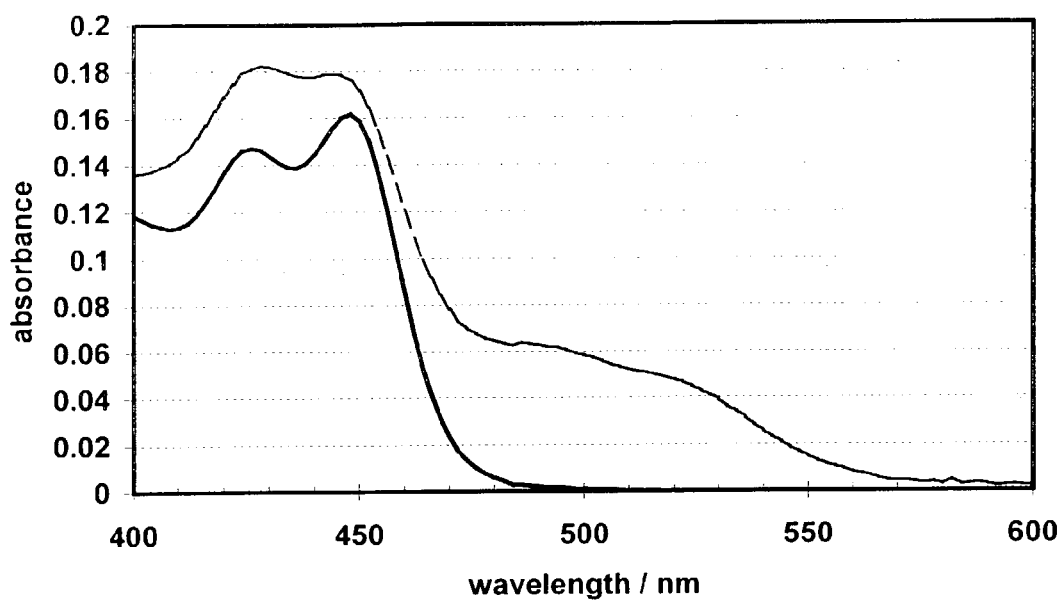
FIG. 3 illustrates the UV-visible absorption spectra of another compound JCc according to the invention in methanol prior to (bold line) and after (thin line) complexation of bicarbonate.
Figure 4:
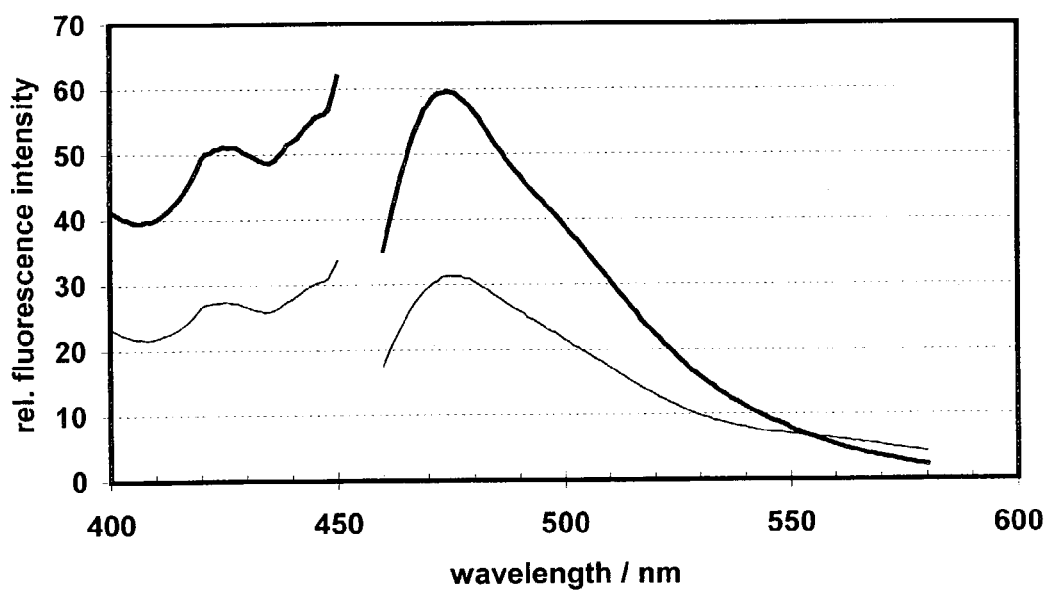
FIG. 4 illustrates the fluorescence spectra of the compound of FIG. 3 in methanol prior to (bold line) and after (thin line) complexation of bicarbonate. Excitation spectra: 400–450 nm, emission 474 nm; emission spectra: 460–580 nm; excitation 448 nm.

A sample of 1.0 mg of JCc was dissolved in 100 mL of methanol. The UV-visible absorption (FIG. 3) and fluorescence (FIG. 4) spectra were taken. An excitation wavelength of 448 nm was used to obtain the emission spectra and an emission wavelength of 474 nm was used to obtain the fluorescence spectra. Then 116.3 mg of sodium bicarbonate was added. The mixture was sonicated for 15 min and allowed to stand for one hour. Then the UV-visible absorption and fluorescence spectra were re-recorded and a 47% decrease in fluorescence intensity was observed.

Example 4

Complexation Studies of Compound JCc with Bicarbonate in Water:Methanol (5:4)

A sample of 1.0 mg of JCc was added to a mixture of 8.0 mL of methanol and 10 mL of 0.1 M pH 7.9 Tris buffer. The UV-visible absorption and fluorescence spectra were taken. An excitation wavelength of 448 nm was used to obtain the emission spectra and an emission wavelength of 479 nm was used to obtain the fluorescence spectra. Then 14.0 mg of sodium bicarbonate was added. Then the UV-visible absorption and fluorescence spectra were re-recorded and a 15% decrease in fluorescence intensity was observed.

Example 5

Complexation Studies of Compound JCd with Bicarbonate in Methanol

Figure 5:
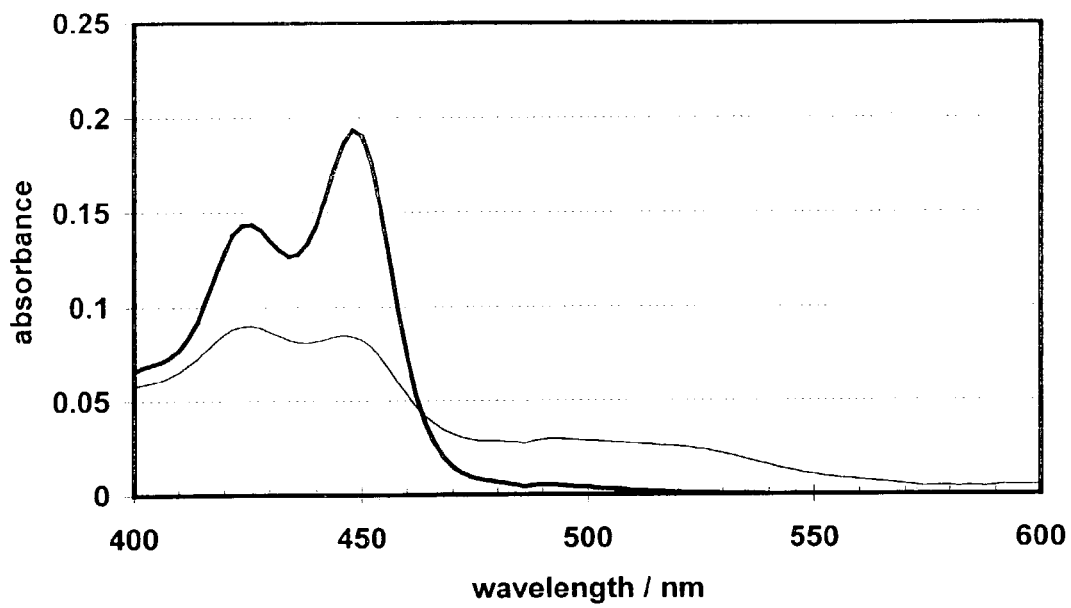
FIG. 5 illustrates the UV-visible absorption spectra of another compound JCd according to the invention in methanol prior to (bold line) and after (thin line) complexation of bicarbonate.
Figure 6:
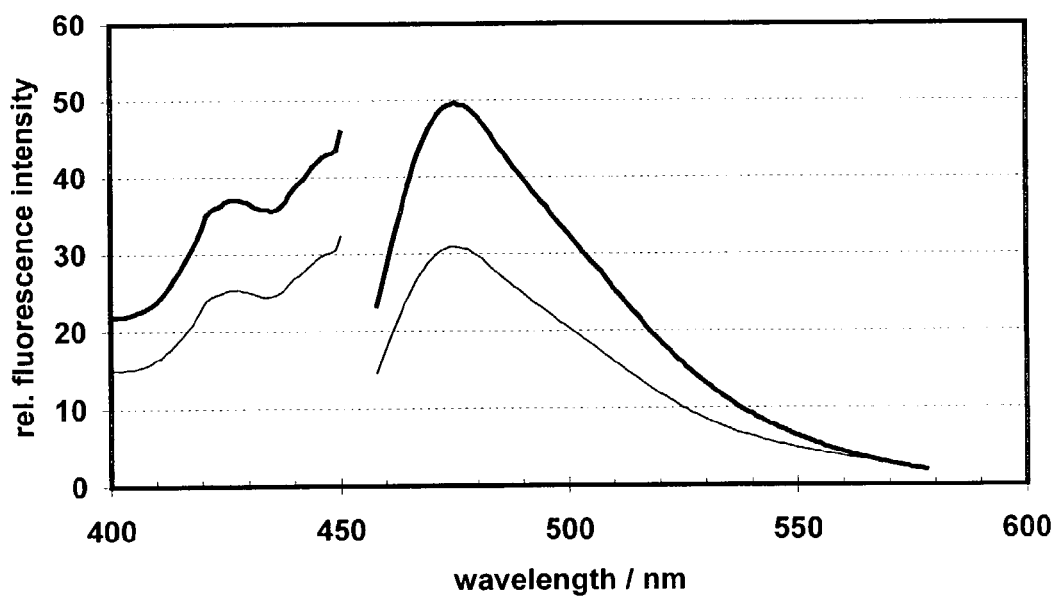
FIG. 6 illustrates the fluorescence spectra of the compound of FIG. 5 in methanol prior to (bold line) and after (thin line) complexation of bicarbonate. Excitation spectra: 400–450 nm, emission 475 nm; emission spectra: 460–580 nm; excitation 451 nm.

A sample of 0.9 mg of JCd was dissolved in 100 mL of methanol. The UV-visible absorption (FIG. 5) and fluorescence (FIG. 6) spectra were taken. An excitation wavelength of 451 nm was used to obtain the emission spectra and an emission wavelength of 475 nm was used to obtain the fluorescence spectra. Then 112.5 mg of sodium bicarbonate was added. The mixture was sonicated for 15 min and allowed to stand for one hour. Then the UV-visible absorption and fluorescence spectra were re-recorded and a 24% decrease in fluorescence intensity was observed.

Example 6

Complexation Studies of Compound JCe with Bicarbonate in Methanol and in Methanol:Water (1:1)

Figure 7:
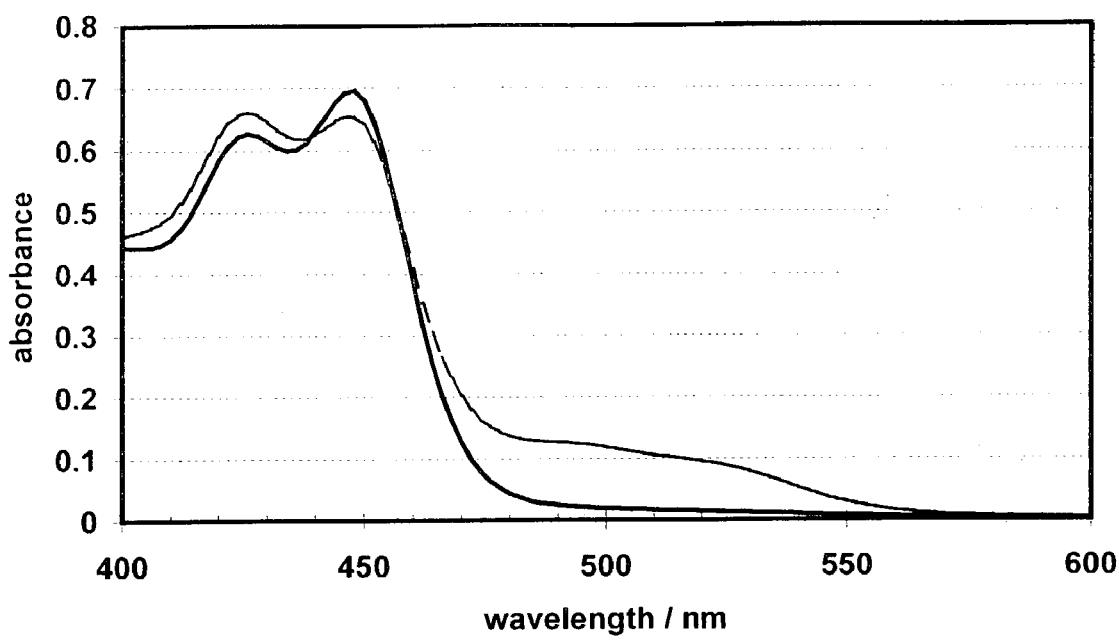
FIG. 7 illustrates the UV-visible absorption spectra of another compound JCe according to the invention in methanol prior to (bold line) and after (thin line) complexation of bicarbonate.
Figure 8:
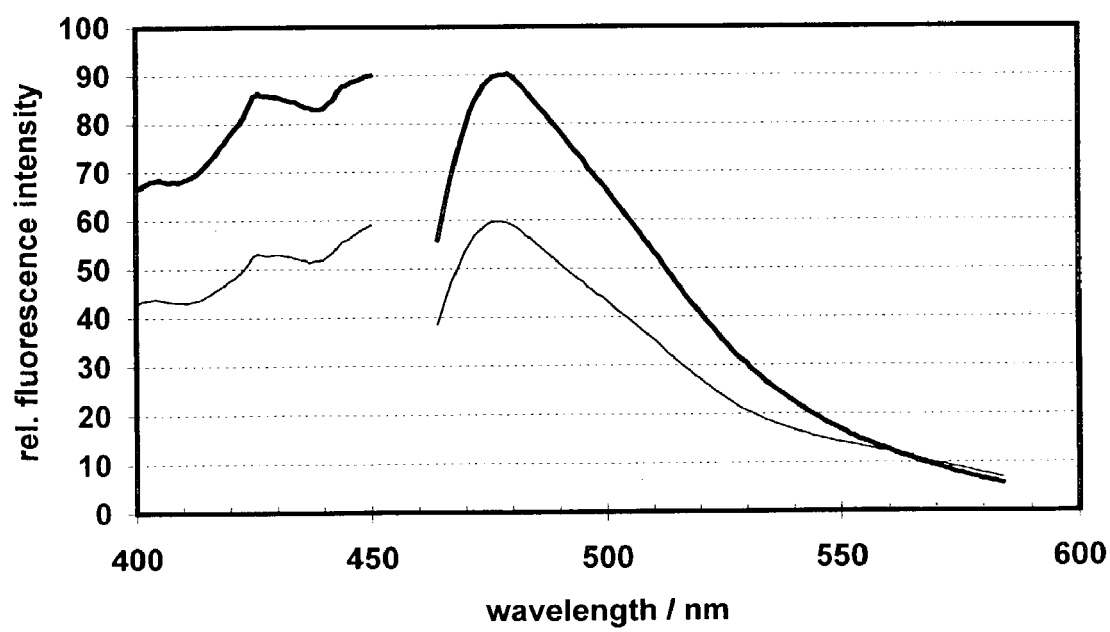
FIG. 8 illustrates the fluorescence spectra of the compound of FIG. 7 in methanol prior to (bold line) and after (thin line) complexation of bicarbonate. Excitation spectra: 400–450 nm, emission 478 nm; emission spectra: 460–580 nm; excitation 448 nm.
Figure 9:
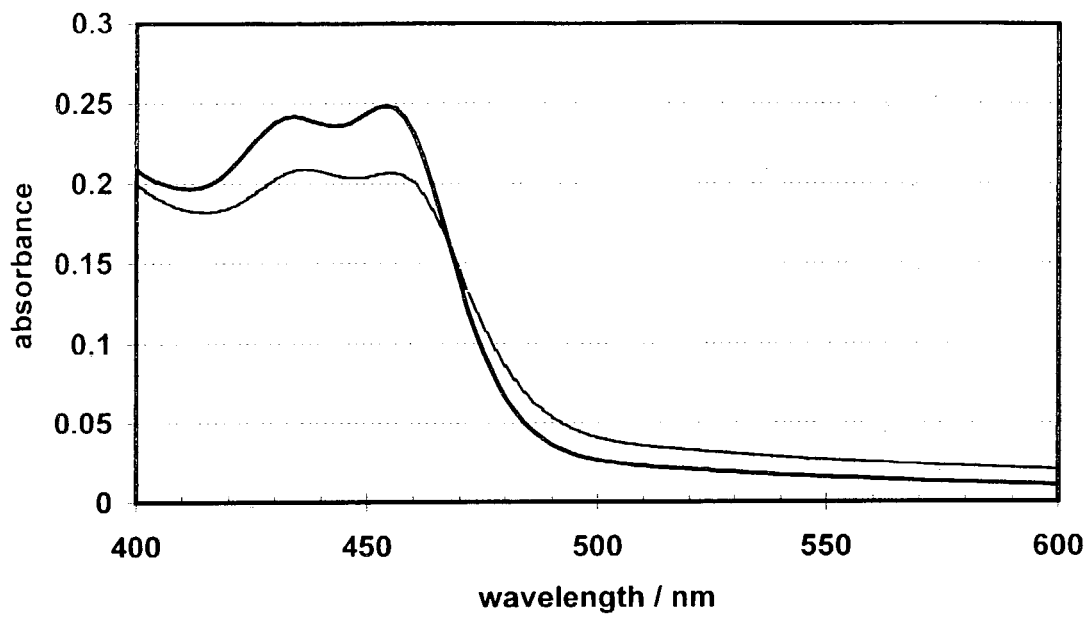
FIG. 9 illustrates the UV-visible absorption spectra of the compound of FIG. 7 in methanol/water=1/1 prior to (bold line) and after (thin line) complexation of bicarbonate.
Figure 10:
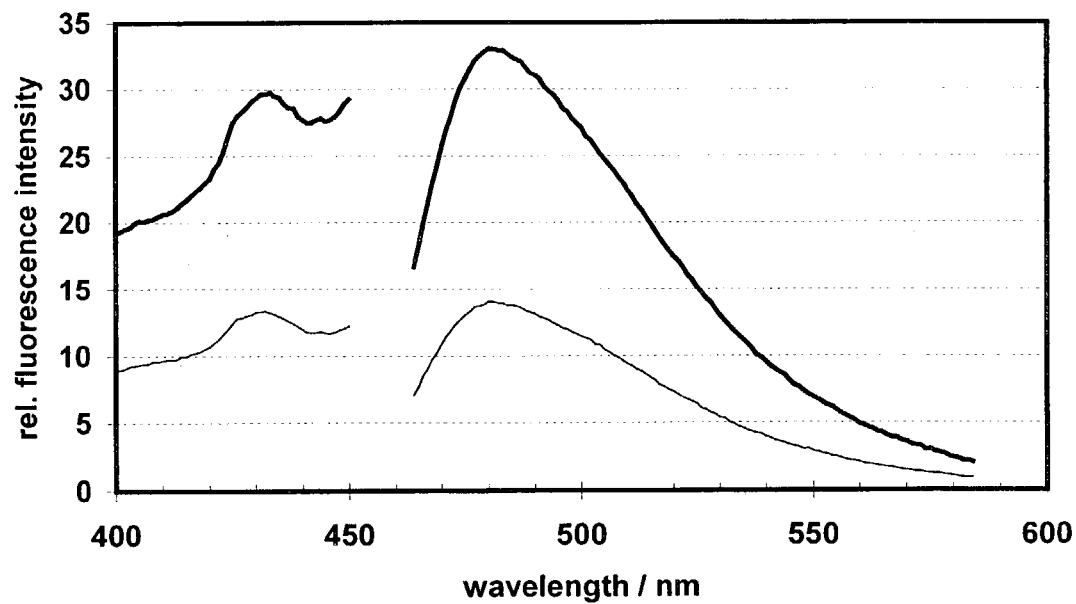
FIG. 10 illustrates the fluorescence spectra of the compound of FIG. 7 in methanol/water=1/1 prior to (bold line) and after (thin line) complexation of bicarbonate. Excitation spectra: 400–450 nm, emission 481 nm; emission spectra: 460–580 nm; excitation 454 nm.

UV-vis absorption (FIG. 7) and fluorescence (FIG. 8) spectra of a solution of JCe in methanol were taken. Then 57.2 mg of sodium bicarbonate was added to 5.0 mL of the solution of JCe in methanol. The mixture was sonicated for 15 min and then allowed to stand for 1 hour. The UV-vis absorption and fluorescence spectra were taken again and a 34% decrease in fluorescence intensity was observed. Then 10 mL of the solution of JCe in methanol was added to 10 mL of 0.1 M pH 8.0 Tris buffer. The UV-vis absorption and fluorescence spectra are shown in FIGS. 9 and 10, respectively. Then 7.3 mg of sodium bicarbonate was added to 8 mL of the solution, which was sonicated for 3 min. The UV-vis absorption and fluorescence spectra were taken. The latter shows a 58% decrease in fluorescence intensity.

Example 7

Bicarbonate Titration of Compound JCe in 0.1 M pH 7.6 Tris Buffer

Figure 11:
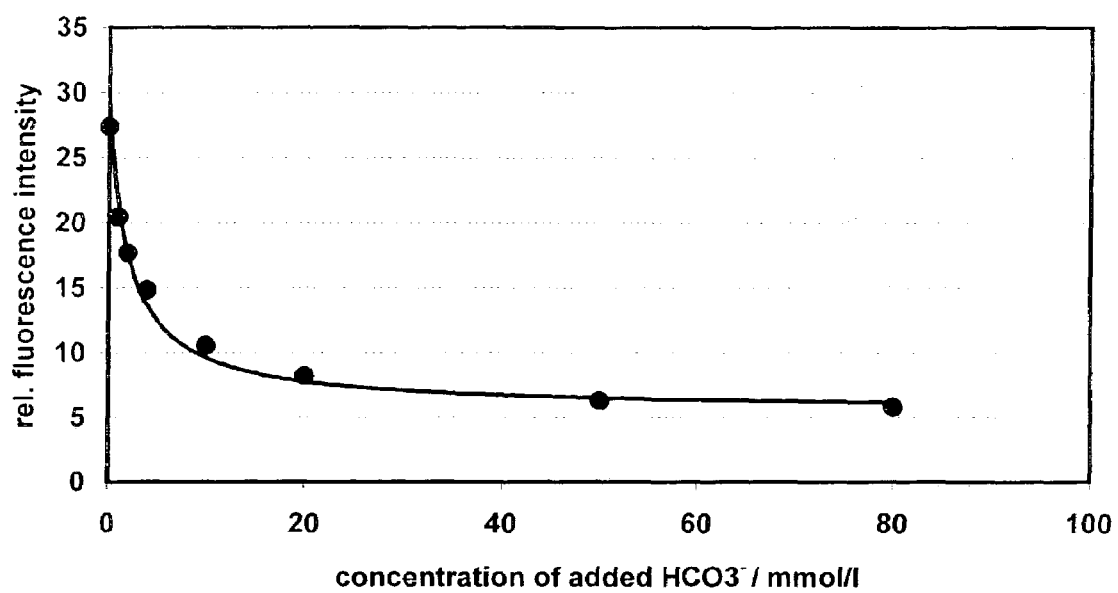
FIG. 11 illustrates the non-linear regression of bicarbonate titration of the compound JCe ($5 \times 10^{-5}$ mol/l) in 0.1 M pH 7.6 Tris buffer. In this medium, the dissociation constant $K_d$ is 2 mmol/l.

To 50 mL of a 5×10$^{-5}$ M solution of JCe in 0.1 M pH 7.6 Tris buffer was added a certain amount of NaHCO$_3$ (solid) each to make different concentrations of bicarbonate. The pH of each solution was checked when the sodium bicarbonate was added. When the pH was higher than 7.6, 1 M hydrochloric acid was added to return the pH to 7.6. The UV-vis absorption and fluorescence spectra were taken. The result gives a maximum 80% decrease in fluorescence intensity and curve fitting by non-linear regression shown in FIG. 11 gives a K$_d$ of 2.0 mM.

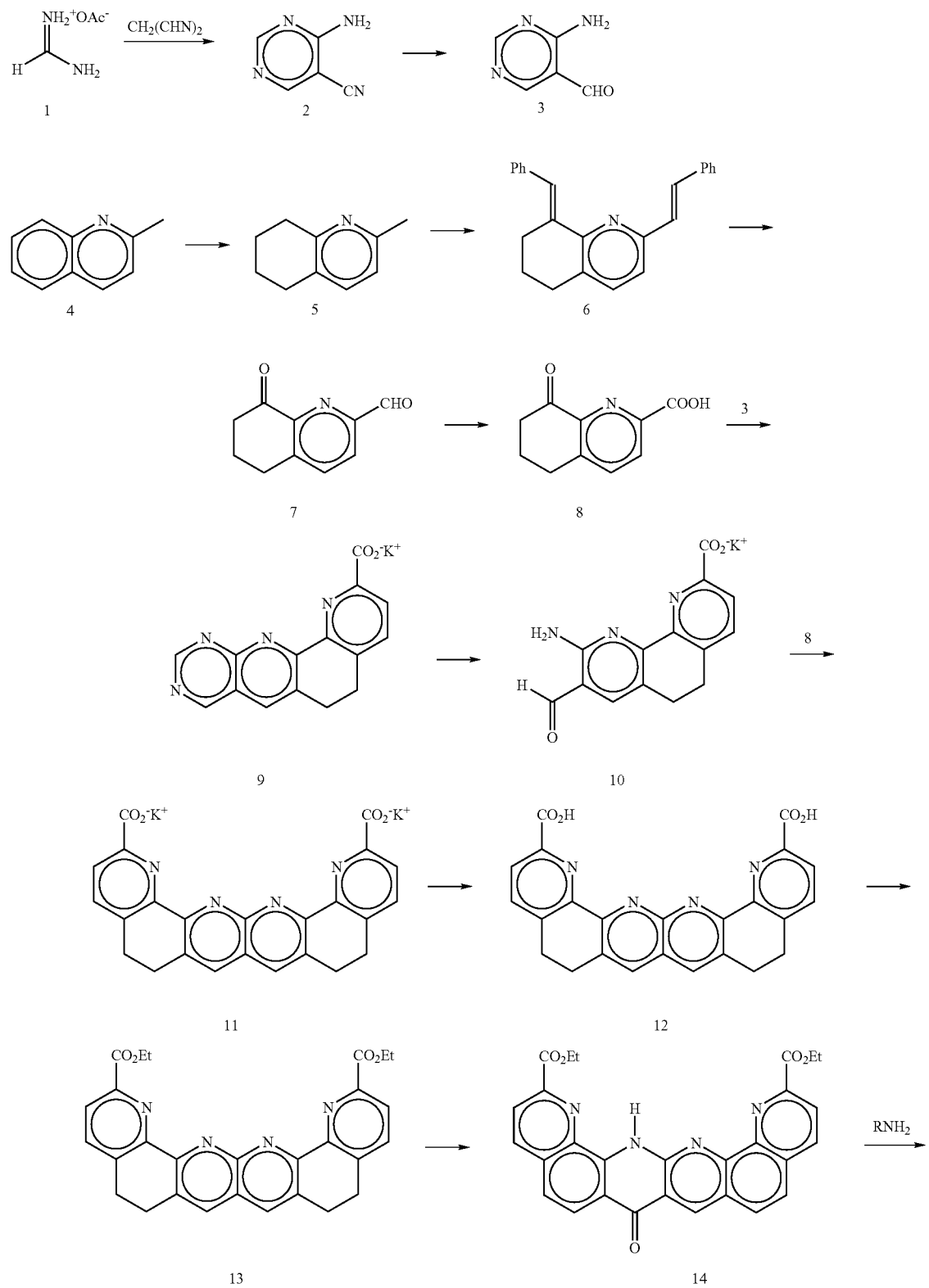
Scheme 1

-continued

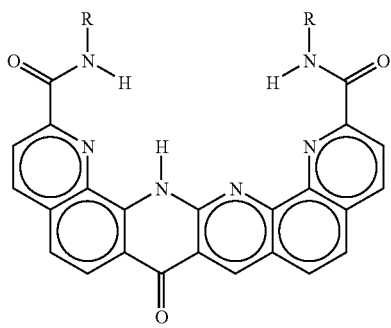

JCb R = C4H9
c R = CH2CH2OH
d R = C8H17
e R = CH2CH2NH2

What is claimed is:

1. A compound having the general formula I

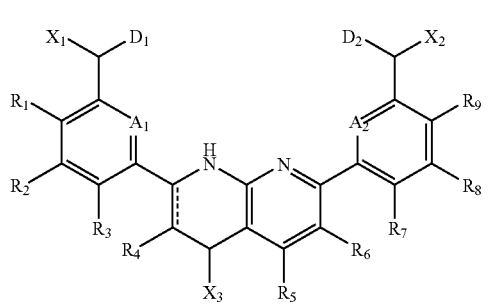

wherein

A$_1$ and A$_2$ are selected from the group consisting of carbon (═CH—) and nitrogen (═N—);

D$_1$ and D$_2$ are selected from the group consisting of —OH, —SH and —NHR$^1$ groups, wherein R$^1$ is hydrogen, hydrophilic substituent, hydrophobic substituent or linker;

X$_1$ and X$_2$ are selected from the group consisting of oxygen (═O), sulphur (═S) and ═NR$^2$ group, wherein R$^2$ is hydrogen, hydrophilic substituent, hydrophobic substituent or linker;

X$_3$ is selected from the group consisting of oxygen (═O), sulphur (═S), ═NR$^2$ group and two singly bonded moieties, wherein both moieties are hydrogen or one moiety is hydrogen and the other moiety is selected from the group of hydrophilic substituent, hydrophobic substituent and linker; and R$_1$–R$_9$ are selected from the group consisting of hydrogen, electron donating substituent, electron accepting substituent, hydrophilic substituent, hydrophobic substituent and linker, or R$_3$ and R$_4$ and/or R$_6$ and R$_7$ form together an aromatic or heteroaromatic, substituted or unsubstituted ring and the remaining moieties R$_1$–R$_9$ are as defined above.

2. A compound according to claim 1, wherein R$_3$ and R$_4$ as well as R$_6$ and R$_7$ each form together an aromatic ring and D$_1$ and D$_2$ are —NHR$^1$ groups, the compound having the general formula II

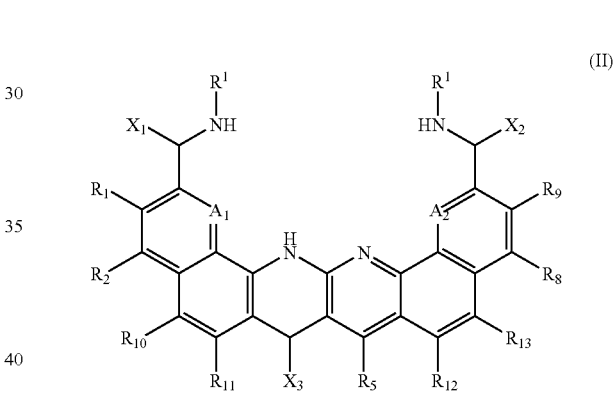

wherein R$_{10}$–R$_{13}$ are selected from the group consisting of hydrogen, electron donating substituent, electron accepting substituent, hydrophilic substituent, hydrophobic substituent and linker.

3. A compound according to claim 2, wherein X$_1$, X$_2$, and X$_3$ are oxygen and R$_1$, R$_2$, R$_5$, R$_8$, R$_9$ and R$_{10}$–R$_{13}$ are hydrogen, the compound having the general formula III

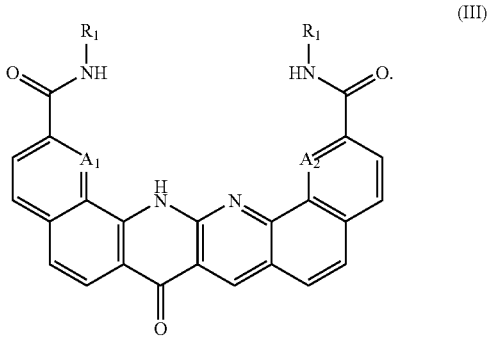

4. A compound according to claim 3, wherein $A_1$ and $A_2$ are nitrogen and $R^1$ is selected from the group consisting of —$C_4H_9$, —$CH_2CH_2OH$, —$C_8H_{17}$ and —$CH_2CH_2NH_2$.

5. A compound according to claim 1, wherein $D_1$ and $D_2$ are —$NHR^1$ groups, the compound having the general formula IV

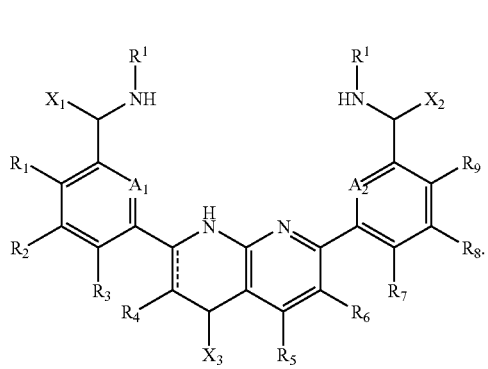

6. A compound according to claim 5, wherein $X_1$, $X_2$, and $X_3$ are oxygen, $A_1$ and $A_2$ are nitrogen and $R_1$–$R_9$ are hydrogen, the compound having the general formula V

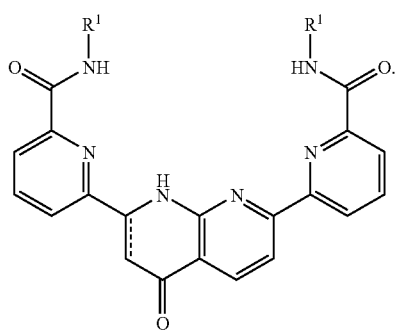

7. A compound according to claim 2, wherein $X_1$, $X_2$, and $X_3$ are oxygen, $A_1$ and $A_2$ are nitrogen, $R_1$, $R_2$, $R_5$, $R_8$, $R_9$ and $R_{10}$–$R_{11}$ are hydrogen, $R^1$ is —$C_4H_9$, $R_{12}$ is hydrogen, an electron donating group or an electron withdrawing group and $R_{13}$ is an electron donating group or an electron withdrawing group, the compound having the general formula VI

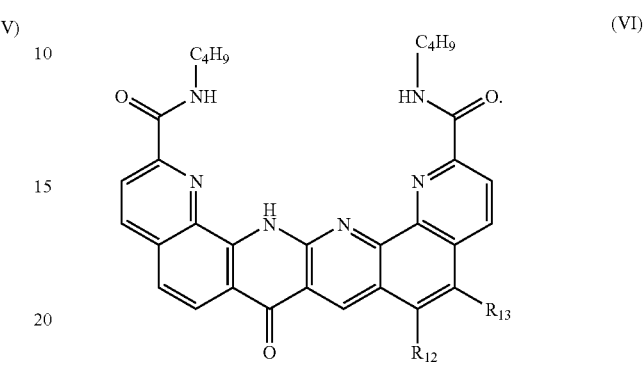

8. A compound according to claim 7, wherein $R_{12}$ is selected from the group consisting of hydrogen, —$NH_2$, —NHR', —OH, —OR', —SH, —SR', —CN, —OAc, —Cl and —$NO_2$ and $R_{13}$ is selected from the group consisting of —$NH_2$, NHR', —OH, —OR', —SH, —SR', —CN, —OAc, —Cl and —$NO_2$, wherein R' is alkyl group, aryl group or linker.

9. A compound according to claim 8, wherein $R_{12}$ is hydrogen and $R_{13}$ is a —$NO_2$ group.

10. A compound according to claim 8, wherein $R_{12}$ is a —$NO_2$ group and $R_{13}$ is hydrogen.

11. An optical sensor for the determination of bicarbonate in a liquid sample comprising
a water impermeable light transmissive support, and
a hydrophilic ion permeable indicator layer comprising the compound of claim 1.

12. An optical sensor according to claim 11 further a comprising a hydrophilic ion permeable light blocking layer.

* * * * *